United States Patent [19]

Kroker et al.

[11] Patent Number: 5,739,195
[45] Date of Patent: Apr. 14, 1998

[54] PROCESS FOR PREPARING AQUEOUS SOLUTIONS OF POLY(N-VINYL-ε-CAPROLACTAM) AND THEIR USE

[75] Inventors: Jörg Kroker, Neustadt; Reinhard Schneider, Fussgönheim; Eberhard Schupp, Grünstadt; Michael Kerber, Weinheim, all of Germany

[73] Assignee: BASF Aktiengesellschaft, Ludwigshafen, Germany

[21] Appl. No.: 809,363

[22] PCT Filed: Sep. 19, 1995

[86] PCT No.: PCT/EP95/03688

§ 371 Date: Mar. 28, 1997

§ 102(e) Date: Mar. 28, 1997

[87] PCT Pub. No.: WO96/10593

PCT Pub. Date: Apr. 11, 1996

[30] Foreign Application Priority Data

Sep. 30, 1994 [DE] Germany .......................... 44 34 986.6

[51] Int. Cl.⁶ .............................. C08F 2/16; C08F 26/06
[52] U.S. Cl. .......................... 524/459; 524/458; 526/264
[58] Field of Search ............................ 524/459, 458; 526/264

[56] References Cited

U.S. PATENT DOCUMENTS 5,126,124  6/1992  Tazi et al. .
5,239,053  8/1993  Tseng et al. ............... 528/483

FOREIGN PATENT DOCUMENTS 0 526 800  7/1992  European Pat. Off. .
1 240 812  11/1967  Germany .
1 285 124  12/1968  Germany .
2 039 079  2/1972  Germany .

OTHER PUBLICATIONS

Hydrophobic Water–Soluble Polymers, 1,Michael Eisele, Walther Burchard Dilute Solution Properties of Poly(1–vinyl–2–piperidone)and poly(N–vinylcaprolactam) Makromol. Chem. 191, 169–184, 1990.

Ullmann's Encyclopedia of Industrial Chemistry Fift, Completely Revised Edition, vol. A21: Plastics, Properties and Testing to Polyvinyl Compounds Editors: Barbara Elvers, Stephen Hawkins, Gail Schulz pp. 754–756.

KHIM. ATSETILENA, 1968 MOSCOW SU, Seiten 382–5, SIDEL'KOVSKAYA, IBRAMIGOV, ASKAROV 'synthesis of graft copolymers of cellulose and poly(n–vinyllactams) siehe Seite 382—Seite 5.

*Primary Examiner*—Joseph L. Schofer
*Assistant Examiner*—Wu C. Cheng
*Attorney, Agent, or Firm*—Oblon, Spivak, McClelland, Maier & Neustadt, P.C.

[57] ABSTRACT

An aqueous solution of poly(N-vinyl-ε-caprolactam) is prepared by polymerizing N-vinyl-ε-caprolactam in an aqueous medium in the presence of a polymerization initiator and from 0.1 to 20% by weight, based on the monomer used, of a water-soluble polymeric protective colloid and is useful as a textile printing adhesive, as a raw material for adhesives, as a lubricant additive, as a cosmetic formulation aid, as a detergent additive and as an opacifier in automatic shading systems.

11 Claims, No Drawings

PROCESS FOR PREPARING AQUEOUS SOLUTIONS OF POLY(N-VINYL-ϵ-CAPROLACTAM) AND THEIR USE

The present invention relates to a process for preparing aqueous solutions of poly(N-vinyl-ϵ-caprolactam) by polymerizing N-vinyl-ϵ-caprolactam in an aqueous medium in the presence of polymerization initiators.

N-Vinyl-ϵ-caprolactam can be prepared for example in an organic solvent or else in water in the presence of free-radical polymerization initiators. The bulk polymerization of N-vinylcaprolactam cannot be realistically contemplated in industry, since the polymerization reaction is difficult to control and the viscosity of the reaction mixture increases rapidly as the polymerization proceeds, so that it is no longer possible to ensure complete mixing. True, the polymerization of N-vinylcaprolactam in an organic solvent is technically feasible, but the organic solvent would have to be removed before any further processing of the polymer. Aqueous solutions of poly(N-vinyl-ϵ-caprolactam) are of particular interest from an application standpoint. However, the polymerization of N-vinyl-ϵ-caprolactam in water is not straightforward because of the thermoreversible solution behavior of the monomer. Vinylcaprolactam monomer has a melting point of 34° C. and is virtually insoluble in cold water, whereas the polymer is readily soluble in cold water, but insoluble in water above the lower critical dissolution temperature of about 35° C. An obvious compromise for the polymerization would be to conduct the reaction at a temperature above the melting point of N-vinylcaprolactam in the manner of an oil-in-water emulsion polymerization. To prepare aqueous polyvinylcaprolactam solutions in this way, the reaction mixture obtained in the oil-in-water emulsion polymerization would have to be stirred with water for a period from several hours to days—especially if the aqueous solution is to have a polymer content of more than 10% by weight—until the viscous or glassy, water-surrounded polymer material turned into a homogeneous solution free of gel particles.

Makromol. Chem. 191 (1990), 169–184, discloses a microemulsion process for polymerizing N-vinyl-ϵ-caprolactam in water in the presence of from about 20 to 50% by weight, based on the monomer, of a dialkyl sulfosuccinate as emulsifier. The disadvantage of such microemulsions is the high emulsifier content.

Poly(N-vinyl-ϵ-caprolactam) is used for example as a polymer additive in lubricant compositions, as a protective colloid and as a binder for nonwovens, cf. Ullmann's Encyclopedia of Industrial Chemistry, Volume A 21, page 754 (1992). DE-B-1 240 812 and DE-A-2 039 079 disclose the use of poly(N-vinylcaprolactam) and mixtures of polyvinylcaprolactam and at least one alkali metal or ammonium salt of a copolymer of at least one acrylic ester, an α,β-monoethylenically unsaturated carboxylic acid and methyl methacrylate as an adhesive for textile material in screen printing. According to U.S. Pat. No. 5,126,124, polyvinylcaprolactam is used in hairsprays. The fact that polyvinylcaprolactam has a thermoreversible solution behavior in water with a lower critical dissolution temperature of about 35° C. makes this polymer interesting for use as an opacifier in automatic shading systems, cf. DE-A-1 285 124.

EP-A-0 526 800 discloses polymers of ethylenically unsaturated compounds containing at least one covalent nitrogen atom in the molecule. They are prepared by free-radical polymerization of the monomers in the presence of monosaccharides, oligosaccharides, polysaccharides or derivatives thereof in aqueous systems. The polymers are useful as film-forming conditioners in cosmetic formulations and as stabilizers for perfumes and perfume oils.

It is an object of the present invention to provide a relatively rapid process for preparing homogeneous aqueous solutions of polyvinylcaprolactam.

We have found that this object is achieved by a process for preparing an aqueous solution of poly(N-vinyl-ϵ-caprolactam) by polymerizing N-vinyl-ϵ-caprolactam in an aqueous medium in the presence of a polymerization initiator, which comprises polymerizing in the presence of from 0.1 to 20% by weight, based on the monomer used, of a water-soluble polymeric protective colloid, polyvinyl alcohol, partially hydrolyzed polyvinyl acetate, polyvinylpyrrolidone, polyacrylamide, polymethacrylamide, carboxylate-functional addition polymers, polyalkyl vinyl ethers and mixtures thereof.

The polymerization according to this invention initially produces suspensions of finely divided polymers in the aqueous medium. Such suspensions have a significantly lower viscosity than aqueous solutions of polyvinylcaprolactam which have the same polymer content. They are readily handleable in industry; that is, they can be completely mixed and readily diluted with water to form ready-to-use solutions having, for example, concentrations of from 0.1 to 50, preferably from 1 to 30%, by weight. The ready-to-use aqueous solutions are preferably prepared by stirring the dilution water required into a polyvinylcaprolactam solution or suspension whose temperature is above the lower critical dissolution temperature of the polymer. Irrespectively, the ready-to-use solutions can also be prepared directly by polymerizing monomer solutions whose concentration corresponds to that of the polymer solutions.

N-Vinyl-ϵ-caprolactam is obtainable for example by vinylation of caprolactam.

Suitable protective colloids for the process of this invention are water-soluble synthetic polymers, for example. Examples of such polymers are polyvinyl alcohol, partially hydrolyzed polyvinyl acetate, polyvinylpyrrolidone, polyacrylamide, polymethacrylamide, carboxylate-functional addition polymers, polyalkyl vinyl ethers and mixtures thereof. Carboxylate-functional addition polymers include for example those formed from ammonium and alkali metal salts of monoethylenically unsaturated $C_3$–$C_5$-carboxylic acids such as acrylic acid, methacrylic acid, maleic acid and itaconic acid. This also includes copolymers of monoethylenically unsaturated carboxylic acids with each other as well as copolymers of monoethylenically unsaturated carboxylic acids with other copolymerizable monomers, such as acrylic esters, methacrylic esters, maleic esters, the esters being derived from alcohols having $C_1$–$C_{18}$-carbon atoms, for example methyl acrylate, ethyl acrylate, isopropyl acrylate, n-propyl acrylate, isobutyl acrylate, n-butyl acrylate, 2-ethylhexyl acrylate, decyl acrylate, dodecyl acrylate and stearyl acrylate, methyl methacrylate, methacrylic acid, ethyl ester and butyl methacrylate. Further suitable comonomers include for example acrylamide, methacrylamide, vinyl acetate, vinyl propionate, vinyl butyrate, acrylonitrile, methacrylonitrile and hydroxyacrylates of monoethylenically unsaturated carboxylic acids, such as hydroxyethyl acrylate, hydroxymethacrylate, hydroxypropyl acrylate, hydroxypropyl methacrylate, hydroxybutyl acrylate and hydroxymethacrylate. The copolymers of monoethylenically unsaturated carboxylic acids can be modified with 2 or else more of the copolymerizable monomers mentioned. The carboxylate-functional addition polymers have a carboxylate group content of from 5 to 100 mol %, for example.

Particular preference is given to using synthetic polymeric protective colloids comprising polyvinyl alcohol and/or partially hydrolyzed polyvinyl acetate having a degree of hydrolysis of from 50 to 99.9 mol %.

Suitable synthetic polymeric protective colloids also include addition polymers of sulfo-containing monomers, for example ammonium or alkali metal salts of homo- or copolymers of 2-acrylamido-2-methylpropanesulfonic acid, acrylamidopropanesulfonic acid, vinylsulfonic acid, allylsulfonic acid and methallylsulfonic acid, and also addition polymers of phosphonic acid monomers, for example ammonium and alkali metal salts of homo- or copolymers of 2-acrylamido-2-methylpropanephosphonic acid, vinylphosphonic acid and allylphosphonic acid.

The polymeric protective colloids which are used according to this invention are termed water-soluble when they are miscible in water in any proportion or have a solubility in 20° C. water of at least 0.1% by weight and do not precipitate from these aqueous solutions on dilution with water at the same temperature. The molecular weight of the water-soluble synthetic polymeric protective colloids is for example from 10,000 to 2,000,000, preferably from 25,000 to 1,500,000. The viscosity of the aqueous solutions of the protective colloids ranges for example from 1 to 10,000 mPas at a concentration of the aqueous solution of from 4 to 10% by weight and a temperature of 20° C.

The process of this invention can also be carried out with water-soluble natural polymers. Substances of this kind include for example gelatin, pectins, alginates, casein, starch, methylcellulose, hydroxypropylcellulose, carboxymethylcellulose or mixtures thereof. Starch can be converted into aqueous solutions by heating in an aqueous medium to temperatures above the gelatinization temperature of the starch. However, the starch can also be degraded, for example oxidatively, hydrolytically or enzymatically. In some cases, it can be of advantage to use mixtures of a synthetic and a natural protective colloid, for example a mixture of polyvinyl alcohol and casein. Further suitable natural polymers are mixed ethers such as methylhydroxyethylcellulose and carboxymethylmethylcellulose.

The amounts of water-soluble polymeric protective colloids which are used in the process of this invention range from 0.1.to 20, preferably from 1 to 5%, by weight, based on the N-vinyl-ε-caprolactam used in the polymerization.

The polymerization of the vinylcaprolactam is effected in an aqueous medium, and the monomer concentration can be up to about 90% by weight and is preferably within the range from 10 to 60% by weight. The polymerization is preferably carried out in pure water, but it can also be carried out in an aqueous medium comprising up to 50% by weight of a water-soluble organic solvent. These solvents are preferably water-soluble polymerization-regulation solvents, for example ethers such as tetrahydrofuran or dioxane, alcohols such as methanol, ethanol, isopropanol and ethylene glycol or glycol ethers such as diethylene glycol or diethylene glycol dimethyl ether. If a regulating water-soluble solvent is used, the amount used is for example from 5 to 50% by weight, based on the monomer used. As well as a regulating organic solvent, customary polymerization regulators can also be used in the polymerization, for example regulating compounds containing sulfur such as mercaptans, for example mercaptoethanol, mercaptopropanol, mercaptobutanol, dodecyl mercaptan, thioglycol, mercaptoacetic acid and mercaptopropionic acid. It is also possible to use allyl compounds such as allyl alcohol and butenols and also aldehydes such as formaldehyde or acetaldehyde. If desired, the polymerization can also be carried out in the presence of a plurality of regulators. If a regulator is used in the polymerization, the amounts used thereof range for example from 0.05 to 20, preferably from 0.1 to 10%, by weight, based on N-vinylcaprolactam.

Suitable free-radical initiators preferably include all those compounds which have a halflife of less than 3 hours at the chosen polymerization temperature. It is also possible to start the polymerization at an initially low temperature and complete it at a higher temperature. In such a case it can be advantageous to use at least two initiators which decompose at different temperatures, in such a way that the polymerization is started with an initiator which decomposes at a low temperature and completed with an initiator which decomposes at a higher temperature. Preference is given to using initiators which are soluble in water or low alcohols such as methanol, ethanol and isopropanol, for example 2,2'-azobis(4-methoxy-2,4-dimethylvaleronitrile), 2,2'-azobis(2,4-dimethylvaleronitrile), 2,2'-azobis(2-methylpropionitrile), 4,4'-azobis(4-cyanovaleric acid), dimethyl 2,2'-azobis(2-methylpropionate), 1,1'-azobis(1-cyclohexanecarbonitrile), 2,2'-azobis(N,N'-dimethyleneisobutyramidine), (1-phenylethyl) azodiphenylmethane, 1-[(1-cyano-1-methylethyl)azo] formamide, 2,2'-azobis(N,N'-dimethyleneisobutyramidine) dihydrochloride or 2,2'-azobis(2-amidinopropane) dihydrochloride, and also acetylcyclohexanesulfonyl peroxide, diacetyl peroxydicarbonate, diisopropyl peroxydicarbonate, t-amyl perneodecanoate, t-butyl perneodecanoate, bis(4-chlorobenzoyl)peroxide, bis(2,4-dichlorobenzoyl) peroxide, t-butyl perpivalate, bis(3,5,5-trimethylhexanoyl)peroxide, dioctanoyl peroxide, diisononanoyl peroxide, didecanoyl peroxide, dilauroyl peroxide, bis(2-methylbenzoyl) peroxide, succinyl peroxide, diacetyl peroxide, dibenzoyl peroxide, di-2-ethylhexyl peroxydicarbonate, dicyclohexyl peroxydicarbonate, t-butyl per-2-ethylhexanoate, t-butyl perisobutyrate and t-butyl permaleate. The choice of the most suitable initiator(s) ultimately follows from the temperature at which the polymerization reaction is to be carried out.

It is also possible, although less preferable, to use redox initiator systems consisting, for example, of peroxide initiators which are cleaved by the addition of reducing agents such as transition metal salts, sodium sulfite, sodium bisulfite, sodium formaldehydesulfoxylate and/or hydrazine or organic compounds such as benzoin, dimethylaniline and ascorbic acid. Such redox initiator systems make it possible to perform the polymerization at temperatures which are distinctly below the decomposition temperature of the peroxide initiators.

Based on N-vinyl-ε-caprolactam, from 500 to 50,000, preferably from 1000 to 20,000, ppm of an initiator or initiator mixture are used, for example.

The polymerization of vinylcaprolactam can be carried out continuously or batchwise. Preference is given to batchwise polymerization in stirred vessels equipped with effective mixing elements such as blade, horseshoe, impeller or propeller stirrers or in other suitable apparatus such as kneaders. The polymerization is customarily carried out in an inert gas atmosphere, for example nitrogen. The temperatures during the polymerization range from around 40° to 150° C., preferably from 60° to 100° C., and the reaction is carried out in pressuretight apparatus under superatmospheric pressure in the case of temperatures which are above the boiling point of the reaction mixture.

The process of this invention gives aqueous solutions of poly(N-vinyl-ε-caprolactam) which, during the polymerization or after the polymerization, are easy to dilute with water to form homogeneous aqueous solutions of a desired concentration. The water can be added continuously, intermittently or all at once. Whereas the prior art preparation of aqueous solutions of polyvinylcaprolactam requires prolonged stirring in water of even finely divided polyvinylcaprolactam, the process of this invention affords aqueous polymer solutions which can be rapidly diluted with water to the desired lower polymer concentration.

A suitable combination of monomer concentration, polymerization temperature, protective colloid, initiator and regulator and also of the concentrations of the starting materials affords poly(N-vinyl-ε-caprolactam) having K values of from 10 to 300, preferably of from 15 to 200 (determined by the method of H. Fikentscher on 1% strength by weight aqueous solutions at 25° C.). The as-polymerized aqueous solutions can be cooled down to temperatures below the lower critical dissolution temperature for polycaprolactam and be rapidly converted, by addition of water, to homogeneous aqueous solutions free from gel and jelly particles.

The aqueous solutions of poly(N-vinyl-ε-caprolactam) are used for example as textile printing adhesive, as raw material for adhesives, as lubricant additive; as cosmetic formulation aids, as detergent additive and as opacifier in automatic shading systems. Cosmetic formulations include for example hair lacquer and hairspray and also skincare cosmetics. The aqueous solutions of polyvinylcaprolactam obtainable by the process of this invention can also be used as assistants in the area of the production, isolation and transportation of petroleum and natural gas, as clarifier in the beverage industry, as detergent additive, as agrochemical assistants, for example as structure improvers for arable soils and for coating seed, for slow-release formulations of drugs or fertilizers, for wastewater treatment and also as assistants in the photo industry.

In the Examples, parts and percentages are by weight. The K values of the polymers were determined by the method of H. Fikentscher, Cellulose-Chemie 13 (1932), 58–63, 71–74, in 1% strength aqueous solution at 25° C.

EXAMPLES

A stirred cylindrical apparatus equipped with a horseshoe stirrer and reflux condenser was charged under nitrogen with the stated amounts of the starting materials mentioned in Table 1, and the contents were heated to 70° or 75° C. with stirring. After the exothermic reaction had ended, the mixture was stirred at a heating-bath temperature of 90° C. for from 0.25 to 2 h.

The comparative examples afforded very viscous to glassy poller materials which were surrounded by water and which could no longer be mixed through by the horseshoe stirrer. The representative examples afforded fluid, readily mixable homogeneous polymer-in-water suspensions.

After the heating bath was removed, either cold water was added continuously over 3 h to set the desired polymer concentration, or the reaction mixture was merely cooled down to room temperature over 1 h. The representative examples did not require any further stirring. The solutions were homogeneous and free from any gel and jelly particles. The polymers prepared by the comparative examples were not readily dilutable with water, but had to be stirred for a prolonged period; cf. the stirring times reported in the table. Only then were the comparative solutions homogeneous. In the case of Comparative Examples 3 and 4, in which sodium bis(2-ethylhexyl) sulfosuccinate was used as emulsifier, an appreciable proportion of undissolved polymer remained attached to the stirring element.

Representative Example 4 and Comparative Example 6 were each carried out in a laboratory kneader.

TABLE

| Examples | | N-vinyl-ε-caprolactam | Water | Protective colloid | Initia- | Monomer concen- |
|---|---|---|---|---|---|---|
| Rep. | Comp. | Parts | parts | Parts a) | tor[b] | tration[c] |
| 1 | — | 300 | 259 | 7.5 A | Y | 46% |
| — | 1 | 300 | 252 | — | Y | 46% |
| 2 | — | 300 | 620 | 7.5 A | Y | 29% |
| — | 2 | 300 | 610 | — Q | Y | 30% |
| — | 3 | 300 | 660 | 15 Q | Y | 28% |
| — | 4 | 300 | 694 | 60 Q | Y | 27% |
| 3 | — | 300 | 685 | 15 A[h] | Z[m] | 29% |
| — | 5 | 300 | 655 | — Z[n] | | 30% |
| 4 | — | 300 | 130 | 30 A[h] | Y[i] | 67% |
| — | 6 | 300 | 130 | — | Y[i] | 67% |
| 5 | — | 300 | 650 | 15 B | Y | 28% |
| 6 | — | 300 | 650 | 15 C | Y | 28% |
| 7 | — | 300 | 650 | 15 D[l] | Y | 28% |
| 8 | — | 300 | 650 | 15 D[m] | Y | 28% |
| 9 | — | 300 | 650 | 15 E | Y | 28% |
| 10 | — | 300 | 650 | 15 F | Y | 28% |
| 11 | — | 300 | 650 | 15 G | Y | 28% |
| 12 | — | 300 | 650 | 15 H | Y | 28% |

| Examples | | Water added[d] | Stirring | Appearance of product | Solids content[e] | Visco | K |
|---|---|---|---|---|---|---|---|
| Rep. | Comp. | Parts | time | at 23° C. | [%] | sity[f] | value[g] |
| 1 | — | 350 | — | homogeneous | 30.4 | 21 s | 71.3 |
| — | 1 | 350 | >24 h | inhomogeneous | 29.4 | 18.5 s | 67.2 |
| 2 | — | — | — | homogeneous | 31.4 | 21 s | 73.7 |
| — | 2 | — | >24 h | inhomogeneous | 18.5 | 17 s | 67.9 |
| — | 3 | — | 12 h | inhomogeneous | 29.1 | 14.1 s | foaming |

TABLE-continued

| | | | | | | | |
|---|---|---|---|---|---|---|---|
| — | 4 | — | — | homogeneous | 30.7 | 11.5 s | 44.0 |
| 3 | — | — | — | homogeneous | 31.1 | 17.5 s | 68.2 |
| — | 5 | — | >24 h | inhomogeneous | 29.1 | 14.5 s | foaming |
| 4 | — | 620 | — | homogeneous | 32.5 | 17.5 s | 73.0 |
| — | 6 | 550 | >5 h | inhomogeneous | 31.1 | 25 s | 78.5 |
| 5 | — | — | — | homogeneous | 30.1 | 18 s | 70.6 |
| 6 | — | — | — | homogeneous | 31.4 | 26 s | foaming |
| 7 | — | — | — | homogeneous | 29.8 | 18 s | 74.3 |
| 8 | — | — | — | homogeneous | 30.4 | 20 s | 74.1 |
| 9 | — | — | — | homogeneous | 30.2 | 26.5 s | 84.0 |
| 10 | — | — | — | homogeneous | 30.4 | 18.5 s | 72.7 |
| 11 | — | — | — | homogeneous | 30.0 | 18 s | 69.1 |
| 12 | — | — | — | homogeneous | 29.9 | 17 s | 67.4 | a)A = partially hydrolyzed polyvinyl acetate, degree of hydrolysis 88 mol %; viscosity (4% strength aqueous solution, 25° C.) 26 mPa · s
B = poly(N-vinylpyrrolidone), K value 90 (1% in water)
C = poly(sodium acrylate), K value 110 (acid form, 1% in water)
D = polyether, cf. l and m
E = polyethyleneimine, molar mass 1.2 million
F = hydroxyethylcellulose, degree of substitution 2.5
G = hydroxypropyl potato starch ether
H = gelatin
Q = sodium bis(2-ethylhexyl) sulfosuccinate
b)Y = 0.5 part of 2,2'-azobis(2-methylpropionitrile) in 100 parts of methanol
Z = 0.85 part of 2,2'-azobis(2-amidinopropane) dihydrochloride in 50 parts of water; solution neutralized with NaOH
c)in the liquor
d)continuously over 3 h
e)after removal of insolubles
f)Ford cup nozzle Ø 4 mm reflux viscosity of a 5.9% strength solution at 23° C.
g)1 % in water
h)partially hydrolyzed polyvinyl acetate, degree of hydrolysis 88 mol %, viscosity (4% strength aqueous solution, 25° C.), 18 mPa · s
i)0.5 part of 2,2'-azobis(2-methylpropionitrile) in 20 parts of methanol
l)polyethylene glycol, M = ca. 35,000
m)polyethylene glycol-polypropylene glycol-polyethylene glycol block copolymer, M = ca. 14,000, HLB = 16
n)addition of 0.3 part of mercaptoethanol as regulator

We claim:

1. A process for preparing an aqueous solution of poly(N-vinyl-ϵ-caprolactam), comprising polymerizing N-vinyl-ϵ-caprolactam in an aqueous medium, wherein the aqueous medium comprises a polymerization initiator and from 0.1 to 20% by weight, based on the weight of the N-vinyl-ϵ-caprolactam, of a water-soluble synthetic polymeric protective colloid selected from the group consisting of polyvinyl alcohol, partially hydrolyzed polyvinyl acetate, polyvinylpyrrolidone, polyacrylamide, polymethacrylamide, carboxylate-functional addition polymers, polyalkylvinyl ethers and mixtures thereof.

2. A process for preparing an aqueous solution of poly(N-vinyl-ϵ-caprolactam), comprising polymerizing N-vinyl-ϵ-caprolactam in an aqueous medium, wherein the aqueous medium comprises a polymerization initiator and from 0.1 to 20% by weight, based on the weight of the N-vinyl-ϵ-caprolactam, of a water-soluble synthetic polymeric protective colloid selected from the group consisting of polyvinyl alcohol, partially hydrolyzed polyvinyl acetate, polyvinylpyrrolidone, polyacrylamide, polymethacrylamide, carboxylate-functional addition polymers, polyalkylvinyl ethers and mixtures thereof,
wherein the water-soluble synthetic polymer is polyvinyl alcohol and/or partially hydrolyzed polyvinylacetate having a degree of hydrolysis of 50 to 99.9 mol %.

3. The process of claim 1, wherein a viscosity of an aqueous solution of said protective colloid ranges from 1 to 10,000 mPas at a concentration of said aqueous solution of form 4 to 10% by weight and at a temperature of 20° C.

4. The process of claim 1, wherein a monomer concentration of N-vinyl-ϵ-caprolactam is up to about 90% by weight.

5. The process of claim 1, wherein a monomer concentration of N-vinyl-ϵ-caprolactam is within the range of from 10 to 60% by weight.

6. The process of claim 1, wherein 1 to 5% by weight, based on the weight of N-vinyl-ϵ-caprolactam, of said water-soluble synthetic polymeric protective colloid is used.

7. The process of claim 1, wherein said aqueous medium is pure water.

8. The process of claim 1, wherein said aqueous medium comprises up to 50% by weight of a water-soluble organic solvent.

9. The process of claim 1, wherein said polymerization initiator is selected from the group consisting of 2,2'-azobis(4-methoxy-2,4-dimethyl-valeronitrile), 2,2'-azobis(2,4-dimethylvaleronitrile), 2,2'-azobis(2-methylpropionitrile), 4,4'-azobis(4-cyanovaleric acid), dimethyl 2,2'-azobis(2-methylpropionate), 1,1'-azobis-(1-cyclohexanecarbonitrile), 2,2'-azobis(N,N'-dimethylene-isobutyramidine), (1-phenylethyl)azodiphenylmethane, 1-[(1-cyano-1-methylethyl)azo]formamide, 2,2'-azobis(N,N'dimethyleneisobutyramidine)dihydrochloride, 2,2'-azobis(2-amidinopropane) dihydrochloride, acetylcyclohexane-sulfonyl peroxide, diacetyl peroxydicarbonate, diisopropyl peroxydicarbonate, t-amyl perneodecanoate, t-butyl perneodecanoate, bis(4-chlorobenzoyl)peroxide, bis(2,4-dichlorobenzoyl) peroxide, t-butyl perpivalate, bis(3,5,5-trimethylhexanoyl)peroxide, dioctanoyl peroxide, diisononanoyl peroxide, didecanoyl peroxide, dilauroyl peroxide, bis(2-methylbenzoyl) peroxide, succinyl peroxide, diacetyl peroxide, dibenzoyl peroxide, di-2-ethylhexyl peroxydicarbonate, dicyclohexyl peroxydicarbonate, t-butyl per-2-ethylhexanoate, t-butyl perisobutyrate, t-butyl permaleate and a mixture thereof.

10. The process of claim 1, wherein poly(N-vinyl-ϵ-caprolactam) having a K value of from 10 to 300 determined by the method of H. Fikentscher on 1% strength by weight aqueous solution at 25° C. is formed.

11. The process of claim 1, wherein poly(N-vinyl-ϵ-caprolactam) having a K value of from 15 to 200 determined by the method of H. Fikentscher on 1% strength by weight aqueous solution at 25° C. is formed.

* * * * *